United States Patent
Morris et al.

(10) Patent No.: US 9,956,350 B2
(45) Date of Patent: May 1, 2018

(54) INJECTION DEVICE

(71) Applicant: Sanofi, Paris (FR)

(72) Inventors: Anthony Paul Morris, Coventry (GB);
William Marsh, Buckingham (GB);
Matthew Jones, Warwick (GB); Joseph Butler, Rugby (GB)

(73) Assignee: Sanofi, Paris (FR)

( * ) Notice: Subject to any disclaimer, the term of this patent is extended or adjusted under 35 U.S.C. 154(b) by 133 days.

(21) Appl. No.: 14/782,725

(22) PCT Filed: Apr. 8, 2014

(86) PCT No.: PCT/EP2014/056966
§ 371 (c)(1),
(2) Date: Oct. 6, 2015

(87) PCT Pub. No.: WO2014/166888
PCT Pub. Date: Oct. 16, 2014

(65) Prior Publication Data
US 2016/0067418 A1 Mar. 10, 2016

(30) Foreign Application Priority Data
Apr. 10, 2013 (EP) ..................... 13163064

(51) Int. Cl.
*A61M 5/00* (2006.01)
*A61M 5/315* (2006.01)
*A61M 5/20* (2006.01)

(52) U.S. Cl.
CPC ...... *A61M 5/31548* (2013.01); *A61M 5/3157* (2013.01); *A61M 5/31551* (2013.01); *A61M 5/20* (2013.01); *A61M 2205/58* (2013.01)

(58) Field of Classification Search
CPC .......... A61M 5/31541; A61M 5/31551; A61M 5/31553; A61M 5/31533; A61M 5/3155;
(Continued)

(56) References Cited

U.S. PATENT DOCUMENTS

| 2002/0007154 A1 | 1/2002 | Hansen et al. | |
| 2003/0160072 A1* | 8/2003 | Geiser | A61M 5/24 222/327 |

(Continued)

FOREIGN PATENT DOCUMENTS

| WO | WO 2002/076539 | 10/2002 |
| WO | WO 2004/078241 | 9/2004 |

(Continued)

OTHER PUBLICATIONS

Rote Liste, "50. Hypophysen-, Hypothalamushormone, andere regulatorische Peptide u. ihre Hemmstoffe," Chapter 50, ed. 2008, 20 pages.

(Continued)

*Primary Examiner* — Emily Schmidt
(74) *Attorney, Agent, or Firm* — Fish & Richardson P.C.

(57) ABSTRACT

A handheld injection device comprising a housing, a piston rod defining a first longitudinal axis and located within the housing, a driver coupled to the piston rod, a dose setting means, which is rotatable about a second longitudinal axis during dose setting, and optionally a power reservoir for driving the driver and/or a release clutch preventing rotation of the driver during dose setting and allowing rotation of the driver during dose dispensing. The first longitudinal axis is spaced from the second longitudinal axis.

21 Claims, 7 Drawing Sheets

(58) Field of Classification Search
CPC .......... A61M 5/31528; A61M 5/31555; A61M 5/31548; A61M 5/3158; A61M 5/31585
See application file for complete search history.

(56) References Cited

U.S. PATENT DOCUMENTS

| | | | | |
|---|---|---|---|---|
| 2004/0092877 | A1* | 5/2004 | Langley | A61M 5/14566 604/151 |
| 2004/0176729 | A1* | 9/2004 | Langley | A61M 5/24 604/207 |
| 2012/0283647 | A1* | 11/2012 | Cronenberg | A61M 5/31535 604/207 |
| 2013/0267908 | A1* | 10/2013 | Leak | A61M 5/19 604/191 |
| 2015/0352288 | A1* | 12/2015 | Andersen | A61M 5/20 604/134 |

FOREIGN PATENT DOCUMENTS

| | | |
|---|---|---|
| WO | WO 2011/039207 | 4/2011 |
| WO | WO 2011/068531 | 6/2011 |

OTHER PUBLICATIONS

International Preliminary Report on Patentability in International Application No. PCT/EP2014/056966, dated Oct. 13, 2015, 7 pages.
International Search Report and Written Opinion in International Application No. PCT/EP2014/056966, dated Jul. 1, 2014, 10 pages.

* cited by examiner

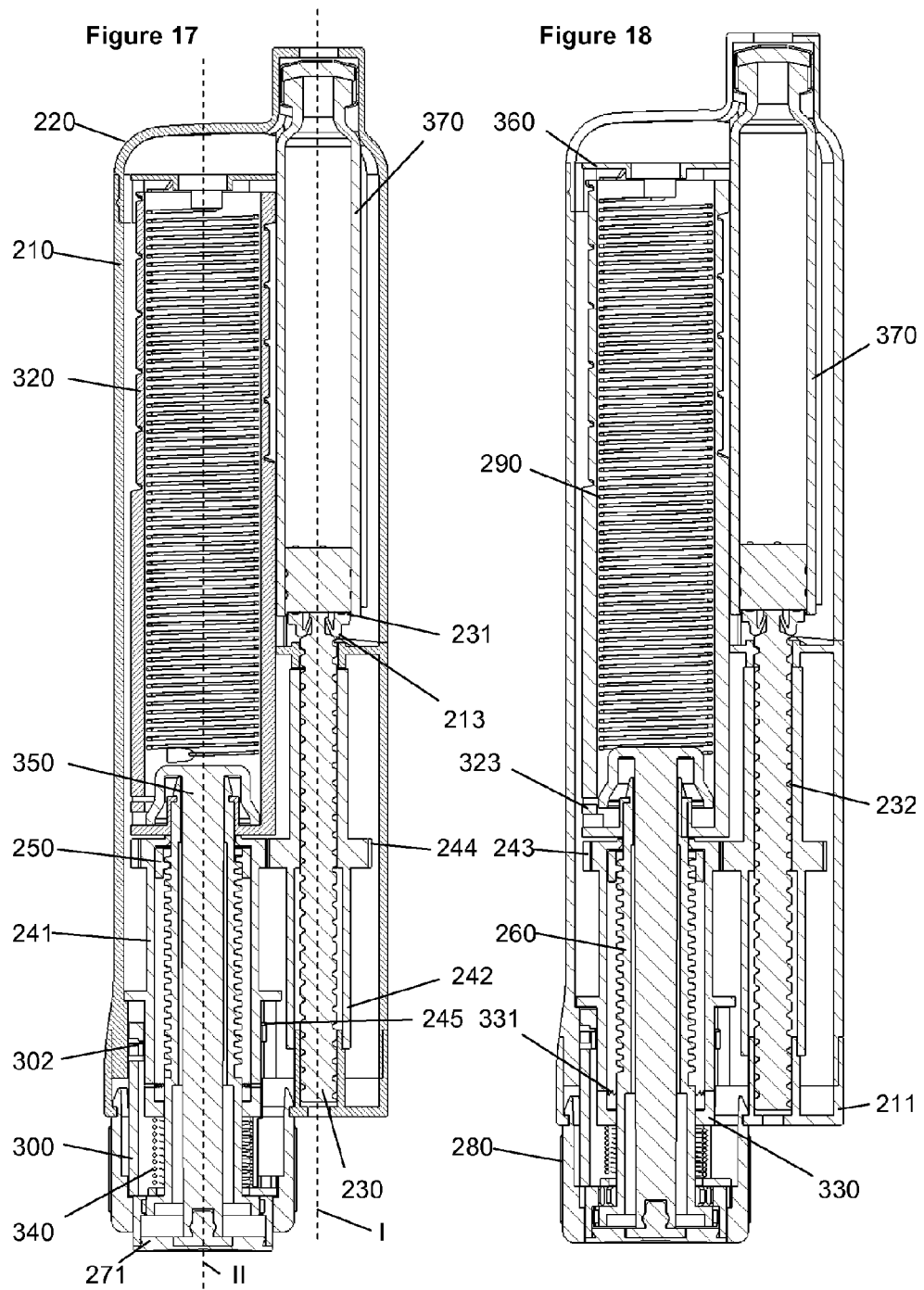

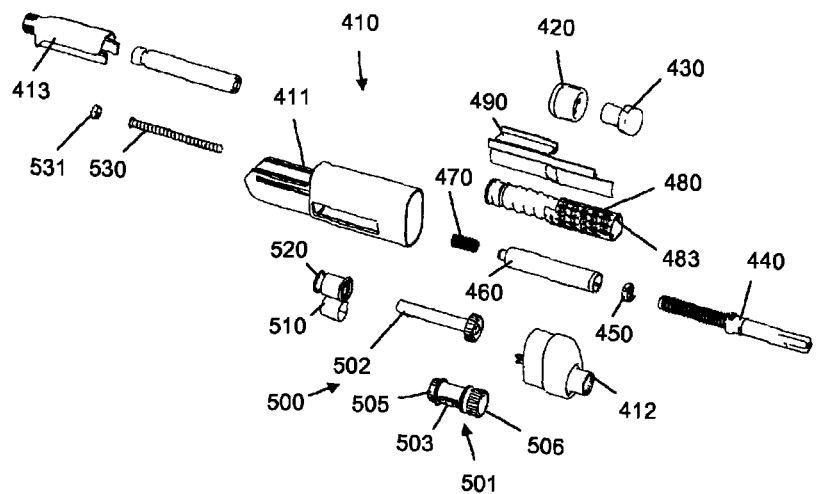
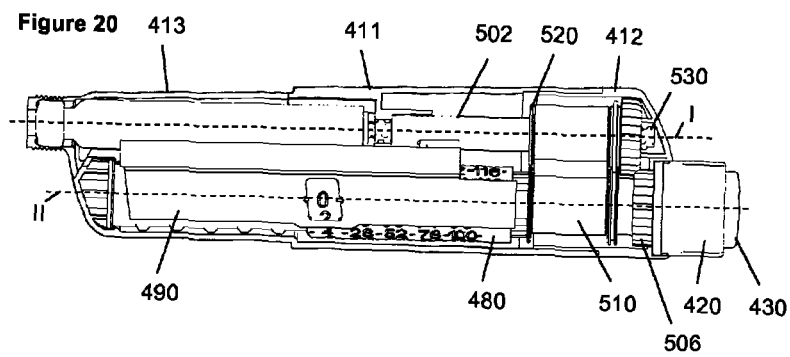

INJECTION DEVICE

CROSS-REFERENCE TO RELATED APPLICATIONS

This application is a § 371 U.S. National Stage Application of PCT/EP2014/056966, filed Apr. 8, 2014, which claims priority to European Patent Application 13163064.2, filed Apr. 10, 2013, the entire contents of which are incorporated herein by reference.

The present invention is generally directed to a handheld injection device, i.e. a drug delivery device for selecting and dispensing a number of user variable doses of a medicament.

Pen type drug delivery devices have applications where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. The present invention is in general applicable for both types of devices, i.e. for disposable devices as well as for reusable devices.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices can involve springs which are (partly) preloaded and springs which are mainly loaded by the user during dose selecting. Some stored-energy devices use a combination of spring preload and additional energy provided by the user, for example during dose setting.

These types of pen delivery devices (so named because they often resemble an enlarged fountain pen) are generally comprised of three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set (select) a dose. During an injection, a spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

A disposable drug delivery device for selecting and dispensing a number of user variable doses of a medicament according to the present invention typically comprises a housing, a cartridge holder for receiving a cartridge, a lead screw or piston rod and means for driving the piston rod during dose dispensing. Such a disposable drug delivery device is known from WO 2004/078241 A1, wherein the cartridge holder is rigidly attached to the device housing. The piston rod, which acts on a cartridge bung, is advanced by a driver during dose dispensing. This known device is a manually driven device, where the component parts are in general disposed concentrically around a common longitudinal axis. During dose setting some component parts wind out of the housing and are pushed back into the housing during dose dispensing.

It is an object of the present invention to provide a drug delivery device with improved user friendliness and handling. It is a further object to make the drug delivery device compact in size, preferably without components translating out of the housing during dose setting.

This object is solved by a device as defined in claim 1.

According to a first embodiment of the present invention the handheld injection device comprises a housing, a piston rod, a driver, a dose setting means, and preferably a power reservoir and/or a release clutch. The piston rod defines a first longitudinal axis and is located within the housing. The driver is coupled to the piston rod. The dose setting means is rotatable about a second longitudinal axis at least during dose setting. The optional power reservoir drives the driver during dose dispensing. The optional release clutch is arranged such that it prevents rotation of the driver during dose setting and allows rotation of the driver during dose dispensing. The first longitudinal axis is spaced from the second longitudinal axis, i.e. there is an offset between the two axes on which the component parts of the device are arranged. Preferably, the first longitudinal axis is parallel to the second longitudinal axis. As an alternative, the two axes may be tapered, but still with an offset between the axes within the device. Due to some of the component parts being located next to others instead of the conventional concentrically arrangement, the cross-section of the device becomes rather elongated than the usual circular pen-shape. This improves handling of the device at least for some users. Further, the device may be made shorter, which again improves handling and convenience. Providing the power reservoir for driving the driver reduces the force required for the user during dose dispensing. This is especially helpful for users with impaired dexterity.

The power reservoir may comprise a spring, which may be a preloaded (pre-charged) spring or a spring which has to be loaded by the user during dose setting, for example a torsion spring. Preferably, the spring is fully pre-charged for the expected life of the device, (reducing the effort required to use the device) i.e. such that a user is not required to re-charge or strain the spring at any time. Suitable spring types include compression springs and torsion springs. According to a preferred embodiment of the invention, the spring is a reverse wound flat spiral spring, which is a band-type spring which is wound up in its charged state counter to its unstressed winding direction. Preferably, a first end of the spring is attached to a first spool, which may be located on the first longitudinal axis, and a second end of the spring is attached to a second spool, which may be located on the second longitudinal axis. For driving the driver, one of the spools may be coupled to the driver, e.g. by means of a direct splined coupling. As an alternative, a releasable coupling may be used, e.g. a pair of teeth rings.

The driver may comprise a tubular element which is coupled to the piston rod. Preferably, this tubular element at least partly surrounds the piston rod. The coupling may be a releasable coupling, however it is preferred that the driver is permanently coupled to the piston rod, e.g. via a splined interface or a threaded interface. A drive tube being a component part of the driver is preferably arranged rotatably about the first longitudinal axis and directly coupled to the piston rod.

The driver may further comprise at least one further component part, for example a drive sleeve which is rotatable about the second longitudinal axis. Thus, two component parts of the driver may be arranged with an offset on parallel axes. Preferably, the component parts of the driver are permanently coupled to each other such that rotation of one component causes rotation of the other component. For example meshing gears might be provided on each of the two driver components. The drive sleeve may be coupled to the power reservoir such that the power reservoir drives the driver components, e.g. via a splined interface. For manufacturing or assembly reasons, the drive sleeve may comprise two or more component parts, which are rigidly connected to each other during assembly such that they act in the device as one component.

According to a further preferred embodiment, the dose setting means comprises a dial assembly and a dial sleeve which are rotatable about the second longitudinal axis. Preferably, the dial assembly is decoupled from the driver during dose setting and, for example a part of the dial assembly like a number sleeve or dose indicator, is coupled to the driver during dose dispensing. However, according to an embodiment of the invention, further parts of the dial assembly, like a dial part, should not be coupled to the drive during dose dispensing. The dial assembly may comprise a dial grip extending at least partially from the housing, which allows a user to select or deselect a dose by rotating the dial grip. The dial grip may further be used as a trigger or release button to initiate dose dispensing. The dial assembly may further comprise a sleeve-like part for interaction with further components. For manufacturing or assembly reasons, the dial grip and the sleeve-like part may comprise two or more component parts, which are rigidly connected to each other during assembly such that they act in the device as one component. Preferably, the dial sleeve may be rotationally coupled and de-coupled with the dial assembly. For example, it is preferred, if rotation of the dial grip is transferred to the dial sleeve during dose setting and/or dose correction, whereas during dose dispensing rotation of the dial sleeve does not entrain the dial grip.

Injection devices usually have a display indicating the current set dose. This might include mechanical displays and electronic displays. Preferably, the device further comprises a number sleeve having a series of numbers and/or symbols on its outside. Typically, a window in the housing allows only the number or symbol corresponding to the current set dose to be viewed from the outside of the device. If the number sleeve is in threaded engagement with the housing and is splined to the dose setting means, the number sleeve may rotate together with the dial sleeve during dose setting (and dose correction) and during dose dispensing. Due to the threaded interface with the housing, the number sleeve travels axially within the housing upon rotation of the number sleeve. Preferably, the number sleeve is rotatable about the second longitudinal axis.

If the piston rod is a threaded lead screw with the housing having a threaded portion cooperating with a threaded outer surface of the piston rod, rotation of the piston rod during dose dispensing results in an axial movement of the piston rod. As an alternative the piston rod may be in threaded engagement with the driver and be splined to the housing.

According to a preferred embodiment, the drug delivery device comprises a limiter mechanism defining a maximum settable dose and a minimum settable dose. Typically, the minimum settable dose is zero (0 IU of insulin formulation), such that the limiter stops the device at the end of dose dispensing. The maximum settable dose, for example 60, 80 or 120 IU of insulin formulation, may be limited to avoid overdosage. Preferably, the limits for the minimum dose and the maximum dose are provided by hard stop features.

The limiter mechanism may comprise a first rotational stop on the number sleeve and a first counter stop on the housing, which abut in the minimum dose (zero) position, and a second rotational stop on the number sleeve and a second counter stop on the housing, which abut in the maximum dose position. As the number sleeve rotates relative to the housing during dose setting and during dose dispensing, these two components are suitable to form a reliable and robust limiter mechanism.

To prevent an underdosage or a malfunction, the drug delivery device may comprise a last dose protection mechanism for preventing the setting of a dose, which exceeds the amount of liquid left in a cartridge. For example, the last dose protection mechanism comprises a nut member located interposed between the driver (or any other component that rotates only during dose dispense) and the dial sleeve or any other component which rotates during dose setting and dose dispensing. In a preferred embodiment, the dial sleeve rotates during dose setting and during dose dispensing, whereas the driver only rotates during dose dispensing together with the dial sleeve. Thus, in this embodiment, the nut member will only move during dose setting and will remain stationary with respect to these components during dose dispensing. Preferably, the nut member is threaded to the dial sleeve and splined to the driver. As an alternative, the nut member may be threaded to the driver and may be splined to the dial sleeve. The nut member may be a full nut or a part thereof, e.g. a half nut.

Initiating dose dispensing usually requires that a user presses a button or trigger. Preferably, at least one component part of the dose setting means and/or the driver is axially displaceable between a dose setting position, in which the dose setting means is rotatable relative to the housing and relative to the driver, and a dose dispensing position, in which the driver is rotatable relative to the housing. The axially displaceable dose setting means may be a dial grip which is used for dose setting. Preferably, the axially displaceable component travels along the second longitudinal axis between its dose setting position and its dose dispensing position.

The sequence of dose setting and dose dispensing usually requires a relative movement of some of the components either during dose setting and/or during dose dispensing. Various different embodiments of achieving this result are possible, some of which are described in the prior art mentioned above. According to a preferred example of the invention, the injection device may further comprise a clutch arranged between the drive member and the number sleeve, wherein the clutch allows relative rotation of the drive member and the number sleeve during dose setting and rotationally constrains the drive member and the number sleeve during dose dispensing. This embodiment may include a relative axial movement during dose setting.

According to a further embodiment of the present invention the handheld injection device comprises a housing, which may contain a cartridge, a dose setting means, which is operable, e.g. rotatable, in a first direction to set a desired dose to be dispensed, a piston rod, which is adapted to cooperate with a piston or bung so as to cause a set dose to be injected from the cartridge, and first and second clicker components. The first clicker component may be rotationally constrained to the housing, whereas the second clicker component may be rotatable relative to the housing during dose dispensing. To provide a non-visual, i.e. an audible and/or tactile, first feedback to a user only close to the end of dispensing of a set dose, the clicker components are adapted to contact each other. If the first clicker component is axially displaceable relative to the housing between a proximal dose setting position and a distal dose dispensing position, the first feedback is generated only if the device is in its dose dispensing mode with the first clicker component being in its distal dose dispensing position. However, if the device is in its dose setting mode with the first clicker component being in its proximal dose setting position, the two clicker components do not engage with each other, thus preventing that a signal or feedback is generated. Thus, dialing up from a minimum dose of zero, will not require any resetting step of the clicker arrangement because no contact occurs between the clicker components.

A further advantage of the first clicker component being axially displaceable relative to the housing between a proximal dose setting position and a distal dose dispensing position, is that the dose setting means may be operable, e.g. rotatable, in a second direction which is opposite to the first direction to cancel a set dose, without the first and second clicker components contacting each other and, thus, without creating the 'end of dose' feedback. This avoids confusion of the users.

Preferably, the injection device further comprises at least one clicker producing an audible and/or tactile feedback during dose setting and/or during dose correction (cancelling of a set dose without dispensing) and/or during dose dispensing. To differentiate between these feedback signals, the first feedback (end of dose dispensing feedback), which is generated only at the end of dispensing of a set dose, is distinct from the further feedback(s). For example, a different sound may be generated.

According to an embodiment of the invention, the second clicker component is a number sleeve, e.g. a tubular element having numbers, symbols or the like on its outer surface, which are visible from the outside of the device, e.g. through a window or aperture in the housing. The number sleeve is preferably in threaded engagement with the housing and splined to the dose setting means.

There are various suitable ways of generating the non-visual, i.e. an audible and/or tactile, feedback signal(s), like a change in a rotational velocity of at least one part, e.g. by changing the pitch of a threaded portion or by engaging a non-rotating part and a rotating part, thereby causing the non-rotating part to start rotating. The feedback may alternatively be generated by building up and releasing a tension. Preferably, the first clicker component has a radially inwards directed protrusion, for example a ramp, and the second clicker component has a flexible element, like a spring arm or finger, which extends radially outwards from the second clicker component. Due to the second clicker component being axially movable, the second clicker component can be positioned such that during dose dispensing the protrusion of the first clicker component contacts the flexible element of the second clicker component. For example, the ramp may flex the spring arm, which snaps back to its unstressed position after disengagement with the ramp, which generates the feedback signal.

To improve handling of the device, the length of the device before and after dose setting is preferably the same. In other words, there is no dial extension due to components winding out of the housing during dose setting. Preferably, the dose setting means and the driver are arranged in the housing such that they are prevented from axial displacement along one of the longitudinal axes during dose setting and during dose dispensing. However, an axial movement of at least some of the components between dose setting and dose dispensing may be possible for switching between a dose setting position and a dose dispensing position of the device.

According to a preferred embodiment, the dose setting means comprises a release button which is axially displaceable along the second longitudinal axis, wherein the device further comprises friction means for decelerating the driver depending on the position of the release button. In other words, a speed control is provided which allows the user to vary the dispensing speed of the device. The friction means may comprise one or more clutch plates or other component parts of the device which are pressed against each other, e.g. by a spring. One of these plates or components rotates during dose dispensing whereas a further of these plates or components is held stationary during dose dispensing. Thus friction is caused by the relative movement of these components which decelerates the device. Pressing the release button decreases the friction, e.g. by lowering the spring force, which thus, leads to an increase of the dispensing speed. The release button may be the dial grip of the dose setting means.

The drug delivery device may comprise a cartridge containing a medicament. Further, a movable bung may be provided in the cartridge.

Usually, injection devices require a so called priming prior to the first use to close a possible gap between the cartridge bung and the piston rod and to overcome tolerances within the device. For the priming step, a user has to set a small dose and to dispense this dose while monitoring whether e.g. fluid leaves the device. This action has to be repeated until e.g. fluid actually leaves the device. According to a preferred embodiment, the piston rod comprises a bearing or tip at its end facing the bung, wherein in the unused delivery state of the device, the bearing abuts the bung. In other words, priming is no longer necessary. This prime elimination may be achieved in a device where the driver is coupled to the piston rod by rotating the driver during the assembly process until the piston rod is moved to a position abutting (and potentially applying a small force to) the cartridge bung. This position may be determined by an increase in the force or torque required to rotate the driver. As an alternative, the axial position of the piston rod relative to the housing or driver may be sensed.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antihousing or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoylLysB28ProB29 human insulin; B30-N-myristoyl-ThrB29LysB30 human insulin; B30-N-palmitoylThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-GlyGlu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antihousing is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antihousing; these chains are found in IgA, IgD, IgE, IgG, and IgM antibodies, respectively.

Distinct heavy chains differ in size and composition; α and γ contain approximately 450 amino acids and δ approximately 500 amino acids, while p and E have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antihousing contains two light chains that are always identical; only one type of light chain, κ or λ, is present per antihousing in mammals.

Although the general structure of all antibodies is very similar, the unique property of a given antihousing is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antihousing fragment" contains at least one antigen binding fragment as defined above, and exhibits essentially the same function and specificity as the complete antihousing of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The present invention provides a mechanism for use in a medical device that can be operated to deliver a number of user variable doses of medicament from a cartridge, via a needle. The device is disposable and is delivered to the user in a fully assembled condition ready for use.

The mechanism uses a motor spring to store energy. This is supplied to the user in a pre-charged state and no subsequent recharging is necessary for the entire life of the device. The user selects the required dose using an input dial and set dose display incorporated into the mechanism. The spring energy is stored until the device is triggered for dispense at which point a proportion of the energy stored is used to deliver the medicament from the cartridge to the user.

Any dose size can be selected between zero and a predefined maximum, in one unit increments. The mechanism permits cancelling of a dose without any medicament being dispensed, by rotation of the dose selection dial (dial grip) in the opposing direction to when selecting a dose.

The trigger is positioned towards the proximal end of the device and, on activation, dispenses medicament if the dose selected is greater than zero.

The device has low torque requirements to set a dose since the spring is pre-charged and low force requirements to trigger dispense of medicament. It has relatively low part count and is particularly attractive for cost sensitive device applications.

The mechanism has the added advantage that several key components are arranged in parallel driven by a gear arrangement. This reduces the overall length of the device.

Non-limiting, exemplary embodiments of the invention will now be described with reference to the accompanying drawings, in which:

FIG. 17 shows a sectional view of the device of FIG. 15 in the dose setting state;

FIG. 18 shows a sectional view of the device of FIG. 15 in the dose dispensing state;

FIG. 19 shows an exploded view of the components of an injection device in accordance with a fifth embodiment of the present invention; and FIG. 20 shows a partially cut away side view of the device of FIG. 19.

Figure 1:
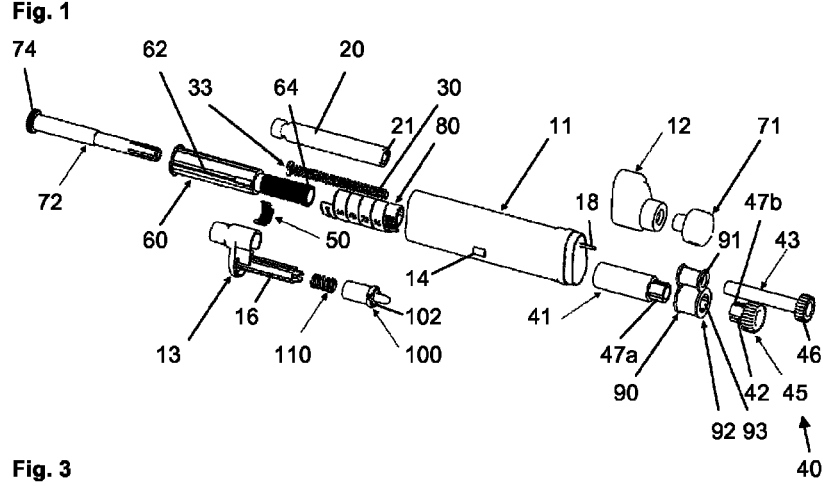
FIG. 1 shows an exploded view of the components of an injection device in accordance with a first embodiment of the present invention.
Figure 2:
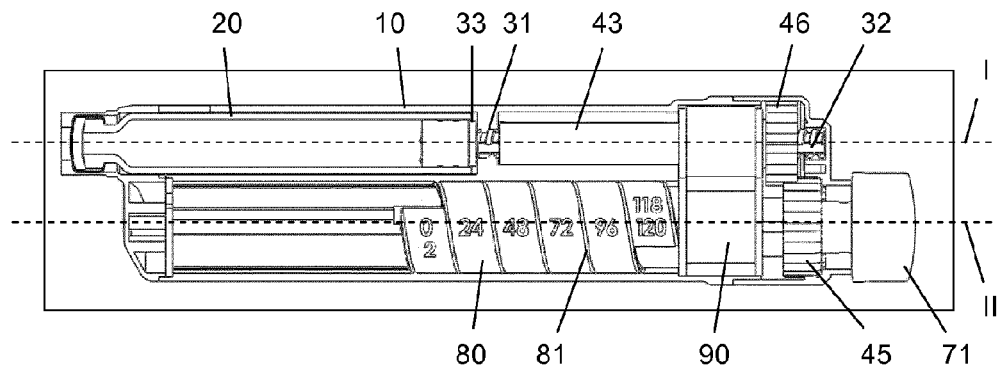
FIG. 2 shows a partial section view of the device of FIG. 1.
Figure 5:
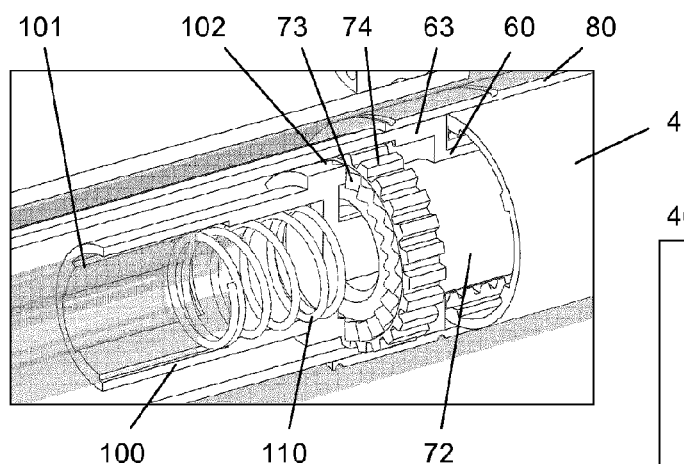
FIG. 5 shows an enlarged view of a detail of the device of FIG. 1.

FIGS. 1 and 2 show a drug delivery device in the form of an injection pen. The device has a distal end (left end in FIG. 2) and a proximal end (right end in FIG. 2). The component parts of the drug delivery device are shown in FIG. 1. The drug delivery device comprises a housing 10, a cartridge 20, a lead screw (piston rod) 30, a driver 40, a nut 50, a dial sleeve 60, a dial assembly 70, a number sleeve 80, a power reservoir (motor spring) 90, a clicker 100 and a spring 110.

A needle arrangement (not shown) with a needle hub and a needle cover may be provided as additional components, which can be exchanged as explained above.

Figure 9:
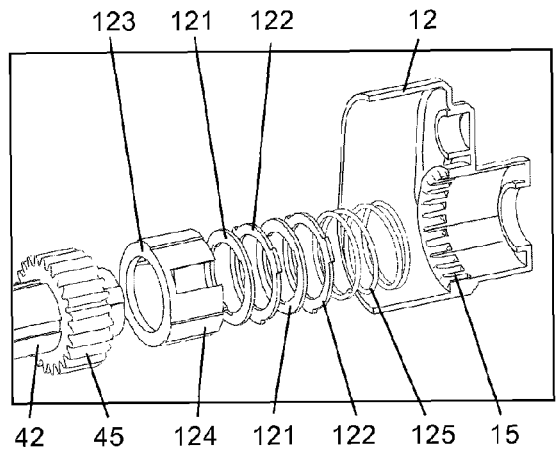
FIG. 9 shows an exploded view of components of an injection device in accordance with a second embodiment of the present invention.

The housing 10 or body comprises a main housing 11, a proximal housing 12 and a distal housing or cartridge holder 13. The main housing 11 is a generally tubular element with an oblong cross section with the lower side in FIG. 1 being widened compared with the upper side. A window 14 or aperture is provided in the main housing 11. The main housing 11, the proximal housing 12 and the cartridge holder 13 can be plugged or snapped together during assembly to close both open ends of the main housing 11. Further, the housing components may be glued or welded together to form a rigid and permanently attached housing unit. The cartridge holder 13 has a distal aperture in its upper region in FIG. 2, which may have an outer thread or the like for attachment of a needle arrangement. The proximal housing 12 has a proximal aperture in its lower region in FIG. 2. Further, the proximal housing 12 has on its inside near the proximal aperture a ring of teeth 15 (shown in more detail in the embodiment of FIG. 9) which forms part of a clutch with the driver 40. The cartridge holder 13 has on its lower side a splined pin 16 for guiding the clicker 100 and spring 110. The housing 10 provides location for the liquid medication cartridge 20, which is held in the upper part (as seen in FIG. 1) of the main housing 11 and the cartridge holder 13.

The main housing has an inner wall with a threaded section 17 engaging piston rod 30. Further, there is a clicker arm 18 near the proximal end of main housing 11, which arm interacts with the driver 40 during dose dispensing.

The cartridge 20 is a glass ampoule with a movable rubber bung 21 located in its proximal aperture.

The lead screw 30 is an elongate member with an outer thread 31 which is rotationally constrained to the driver 40 via a splined interface. The interface comprises at least one longitudinal groove or track 32 and a corresponding protrusion or spline 44 of the driver 40. When rotated, the lead screw 30 is forced to move axially relative to the driver 40, through its threaded interface 17 with the housing 10. The distal end of the piston rod 30 is provided with a bearing 33, which may abut the cartridge bung 21.

The driver 40 comprises a drive sleeve, which has for manufacturing reasons a drive sleeve lower part 41 and a drive sleeve upper part 42, and a drive tube 43. The drive sleeve lower part 41 and the drive sleeve upper part 42 are rigidly connected to form a unit when in use. The drive tube 43 is arranged on a first longitudinal axis I and the drive sleeve is arranged on a second longitudinal axis II, which is parallel to and spaced from the first axis I.

On the inside of the drive tube 43, splines 44 are provided engaging corresponding grooves 32 of the piston rod 30. The drive tube 43 surrounds the piston rod 30 which is axially displaceable relative to the drive tube 43. As shown in FIGS. 1 to 4, the drive sleeve upper part 42 and the drive tube 43 each have at their proximal end a pinion 45, 46, which mesh such that rotation of the drive sleeve 41, 42, is transmitted to the drive tube 43. The drive sleeve 41, 42, is axially movable along the second axis II between a proximal position (during dose setting and correcting, see FIG. 3) in which pinion 45 further engages teeth 15 of the housing 10, and a distal (dose dispensing position, see FIG. 4) in which the pinion 45 is disengaged from the teeth 15. However, in both axial positions pinions 45, 46 remain in at least partial engagement.

The drive sleeve 41, 42, has on its outer surface splines 47a, 47b for rotationally constraining the drive sleeve to the power reservoir 90. Further, splines 48 are provided on the inner surface of the drive sleeve 41, 42, for rotationally constraining the drive sleeve 41, 42, to nut 50.

The nut 50 is part of a last dose limiter mechanism. The last dose nut 50 is located between the dial sleeve 60 and the drive sleeve 41, 42. It moves along a helical path relative to the dial sleeve 60, via a threaded interface 61, when relative rotation occurs between the dial sleeve 60 and drive sleeve during dialling, i.e. during dose setting or dose correcting. In the embodiments of FIGS. 1 to 11, the nut 50 is a half nut, i.e. a component extending approximately 180° around the second axis II of the device.

The dial sleeve 60 is a tubular element arranged rotatably on the second axis II. A proximal section of the dial sleeve 60 is provided with a thread 61 guiding the nut 50. An adjacent distal section is provided with outer splines 62 for engagement with the number sleeve 80. Further, the dial sleeve 60 has a ring of inner teeth 63 at an intermediate stepped portion for releasably rotationally coupling the dial sleeve 60 to the dial assembly 70. Outer splines 64 are provided at the proximal end for engaging corresponding inner splines of the driver 40 during dose dispensing.

The dial assembly 70 comprises dial grip 71 and a tubular element 72 which is rigidly attached to the dial grip 71. The dial grip 71 and the tubular element 72 are in the present embodiment separate components for manufacturing reasons but may as well be a single component. The dial assembly 70 is arranged on the second axis II and extends through the proximal aperture in the proximal housing part 12. At its distal end, the dial assembly is provided with a ring of detent teeth 73 on its distal face for interaction with clicker 100. Further, splines 74 are provided near the distal end of tubular element 72 engaging splines 63 in the dose setting position. The dial assembly 70 is axially movable along the second axis II between a proximal position (during dose setting and correcting, see FIG. 3) and a distal (dose dispensing position, see FIG. 4). The dial grip 71 abuts the drive sleeve 41, 42, such that axial movement of the dial grip 71 in the distal direction entrains the drive sleeve 41, 42, and axial movement of the drive sleeve 41, 42, in the proximal direction entrains the dial grip 71.

The number sleeve 80 is a tubular element arranged on the second axis II. The outer surface of the number sleeve 80 is provided with a sequence of numbers arranged on a helical path. Further, the number sleeve has on its outer surface a thread 81 engaging a corresponding thread of the main housing 11. At its distal end, the number sleeve 80 is provided with an inwardly directed protrusion 82 for interaction with the clicker 100. Further, there are rotational hard stops on the number sleeve 80 and corresponding elements on the main housing 11 limiting the rotational movement of the number sleeve relative to the housing on its helical path defined by the threaded interface.

The power reservoir comprises a reverse wound flat spiral spring 90, that is a bandlike spring, which has a spiral form in its unstressed condition and is wound counter to that unstressed spiral direction for tensioning the spring. A first end of the spring 90 is attached to a first spool 91, which is located on the first longitudinal axis I surrounding drive tube 43. A second end of the spring 90 is attached to a second spool 92, which is located on the second longitudinal axis II and is rotationally constrained to the drive sleeve 41, 42, by splines 47a, 47b and corresponding grooves 93 inside the second spool 92. Spring 90 is fully charged (tensioned) during assembly of the device by winding the spring on spool 92, whereas the spring tends to wind back on spool 91. The power reservoir is dimensioned such that spring 90 is able to drive the piston rod 30 from its retracted position shown in FIGS. 2 to 4 to a position, where the cartridge bung is pushed in its most distal direction. In other words, recharging of the spring 90 is not necessary for emptying cartridge 20.

Figure 8A:
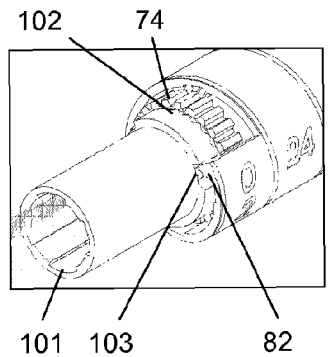
FIG. 8a shows an enlarged view of a detail of the device of FIG. 1 in the dose dispensing state.
Figure 8B:
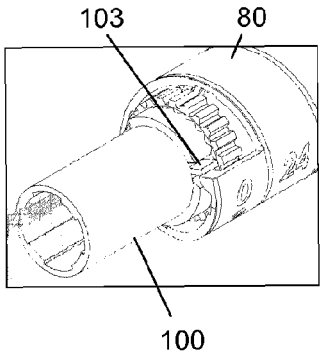
FIG. 8b shows an enlarged view of a detail of the device of FIG. 1 in the dose dispensing state.
Figure 8C:
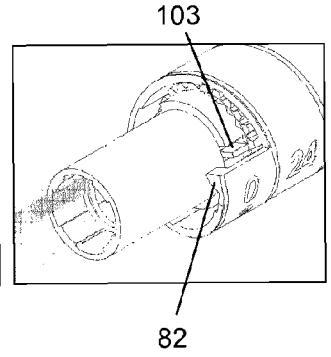
FIG. 8c shows an enlarged view of a detail of the device of FIG. 1 in the dose setting state.

The clicker 100 is a tubular element positioned axially displaceable but rotationally constrained on splined pin 16 of the cartridge holder 13. As can be seen in FIGS. 8a to 8c, the clicker 100 has grooves 101 on its inner surface for engagement with the splined pin 16. Further, there are detent teeth 102 on the proximal end of clicker 100 mating with teeth 73 of the dial assembly 70. A finger 103, which interacts with protrusion 82 of the number sleeve, is provided near the detent teeth 102.

Figure 3:
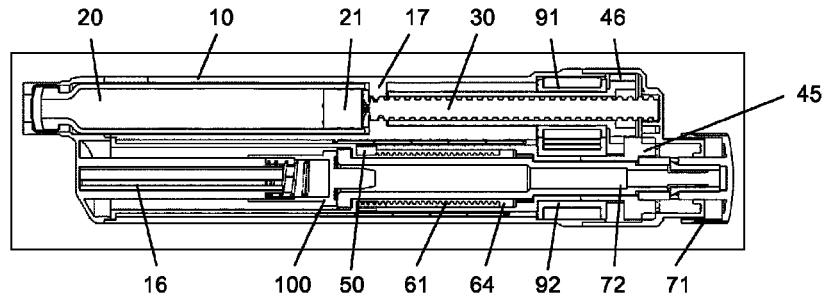
FIG. 3 shows a sectional view of the device of FIG. 1 in the dose setting state.
Figure 4:
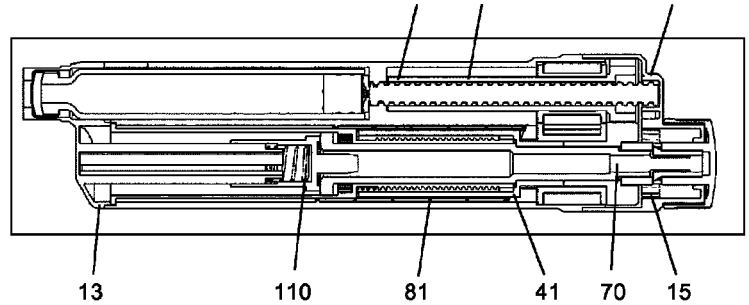
FIG. 4 shows a sectional view of the device of FIG. 1 in the dose dispensing state.

Spring 110 is a compression spring located on splined pin 16 and inside clicker 100 urging clicker 100 in the proximal direction. Due to the contact between the clicker 100 and the dial assembly 70 and due to the contact between the dial assembly 70 and the drive sleeve 41, 42, the spring 110 pushes these components in the proximal direction as shown in FIG. 3, whereas a user may overcome the spring 110 force and push these components in the distal position shown in FIG. 4.

In the following, the functioning of the disposable drug delivery device and its components will be explained in more detail.

Rotation of the dial grip 71 causes the number sleeve 80 to travel between the 0U and 120U stops in the housing 10. There is an axial detent toothed interface between the clicker 100 and tubular element of the dial assembly 70 (which are forced together by the spring 110) which generates the detented dose positions and user feedback. The drive sleeve 41, 42 is rotationally restrained during dialling via a splined interface to the housing 10.

The key interfaces during dialling are: the dial sleeve 60 is splined to the dial grip 71, the number sleeve 80 is splined to the dial sleeve 60, the number sleeve 80 is threaded to the housing 10, the clicker 100 is splined to the cartridge holder 13 10, the drive sleeve 41, 42 is splined to the splined pin 16, the nut 50 is threaded to the dial sleeve 60, and the nut 50 is splined to the drive sleeve 41, 42.

The zero and maximum dose stops are generated by abutments between the number sleeve 80 and housing 10. User input torque, applied to the dial grip 71, is reacted via the dial sleeve 60 and number sleeve 80 back to the housing 10 when the abutments are engaged.

The nut 50 advances towards a rotational abutment at the proximal end of the dial sleeve 60 whilst there is relative rotation between the dial sleeve 60 and drive sleeve 41, 42. When the abutment is reached, dial torque is reacted through the dial grip 71, dial sleeve 60, nut 50 and drive sleeve 41, 42 back to the splined interface with the housing 10.

To dispense a dose, the dial grip 71 is pressed by the user. It then disengages from the dial sleeve 60, and is rotationally constrained by the clicker 100 detent teeth engagement (between the tubular element 72 of the dial assembly 70 and the clicker 100). Axial force applied by the user is reacted by the spring 110, and by a direct abutment between the dial grip 71 and the housing 10. As the dial grip 71 is rotationally decoupled from the mechanism during dispensing, the user is unable to input abuse torques to the dispensing mechanism or adjust the dose.

The drive sleeve 41, 42 is moved axially so that it first engages spline features 64 with the dial sleeve 60 then disengages from its splined interface 45, 15, with the housing 10. The spring 90 then causes the drive sleeve 41, 42 to rotate. Via the geared interface between the drive sleeve 41, 42 and the drive tube 43, the drive tube 43 is rotated which then drives the piston rod 30 through the housing 10 into the bung 21. The drive sleeve 41, 42 causes the number sleeve 80 to rotate back towards the 0U position, via the dial sleeve 60.

The key interfaces during dispensing are: the drive sleeve 41, 42 is axially constrained to the dial grip 71 and displaced towards distal end of the device, the dial grip 71 disengages from the dial sleeve 60, the drive sleeve 41, 42 engages with splines on the dial sleeve 60, and the drive sleeve 41, 42 disengages from the housing 10.

Dispensing of a dose continues until the number sleeve 80 reaches its 0U abutment with the housing 10, or the user releases the dial grip 71. When the 0U abutment engages, torque from the spring 90 is reacted via the dial sleeve 60 and number sleeve 80 into the housing 10. If the user releases the dial grip, the action of the spring 110 acts to re-engage the splined interface 15, 45, between the drive sleeve 41, 42 and housing 10.

Feedback during dose setting is provided by an interaction between the tubular element of the dial assembly 70 and the clicker 100. The clicker 100 is splined to the cartridge holder 13 splined pin 16, and the spring 110 forces the clicker 100 into axial engagement with the tubular element of the dial assembly 70. Detent teeth 73, 102 provide an axial detent toothed interface between the components and the clicker 100 shuttles axially as the dial grip 71 is rotated, providing detented positions for the dial grip. This is shown in more detail in FIG. 5, where splines 74 of tubular element 72 are shown disengaged from the inner ring of splines 63 of the dial sleeve 60, i.e. the device is in its dose dispensing position. Further, teeth 73 and teeth 102 are shown.

Figure 6:
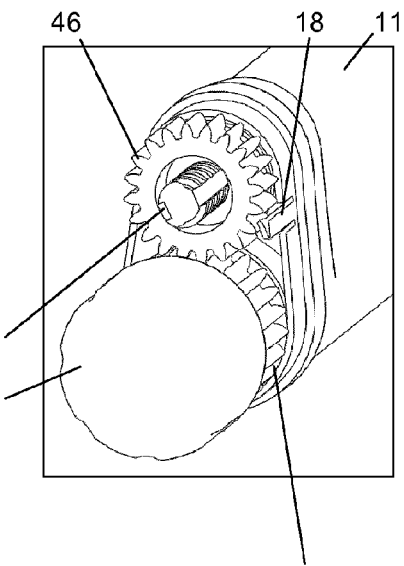
FIG. 6 shows an enlarged view of a detail of the device of FIG. 1.
Figure 7:
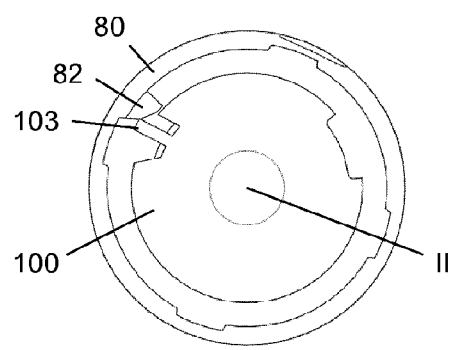
FIG. 7 shows an enlarged view of a detail of the device of FIG. 1.

During dose dispense, tactile and audible feedback is created by the interaction of the drive tube 43 and the housing 10. As shown in FIG. 6, there is a compliant clicker arm 18 integrated into the main housing 11 which is displaced by rotation of the gear teeth 46 on the drive tube 43. The clicker arm 18 contacts the surface of the proximal housing 12 as the gear teeth 46 pass over the clicker arm 18, generating feedback for each dose unit dispensed.

At the completion of the delivery of a dose, as the number sleeve 80 returns to its 0U position, additional audible feedback is created by the interaction of the number sleeve 80 and the clicker 100. As shown in FIGS. 8a to 8c, this interaction is dependent on the axial position of the clicker 100, and only occurs during dispense, when the clicker 100 is in its distal position, when the dial grip 71 is depressed by the user. By utilising the axial position of the dial grip to create this interaction, the end of dose feature does not need to be overhauled by the user during dialling of a dose (see FIG. 8c).

In this embodiment, a radial finger 103 extends from the clicker 100, and a protrusion in the form of a ramped boss 82 is added to the inner surface of the number sleeve 80, such that the boss on the number sleeve 80 deflects the radial finger 103 as the number sleeve 80 rotates back from the 1U position (shown in FIG. 8a) to the 0U position (shown in FIG. 8b). As the number sleeve 80 returns to the 0U position, the radial finger 103 is released and springs back to its at rest state creating audible feedback to the user. As the clicker 100 is in direct contact with the dial assembly, tactile feedback will also be provided, as the dial grip will be being held in its depressed state by the user.

It is possible to incorporate a mechanism that allows the user to control the speed of dispense by the degree of travel that they input to the dial grip 71. The second embodiment shows in FIGS. 9 to 10b a multi-plate clutch system 120 integrated into the device acting between the housing 10 and the drive sleeve 41, 42. This system comprises first clutch plates 121, which are splined to the upper drive sleeve 42, and second clutch plates 122 which are splined to a cage 123. The cage 123 has outer splines 124 engaging with corresponding grooves in the proximal housing 12 to rotationally constrain cage 123. A clutch spring 125 is interposed between the proximal housing 12 and the clutch plates 121, 122 within the cage 123.

Figure 10A:
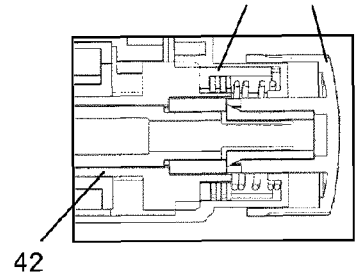
FIG. 10a shows a view of a detail of the device of FIG. 9 in the dose setting state.
Figure 10B:
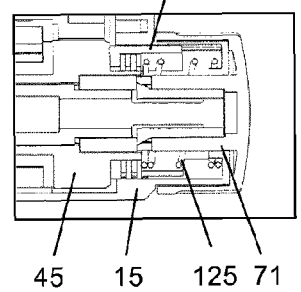
FIG. 10b shows a view of a detail of the device of FIG. 9 in the dose dispensing state.
Figure 11:
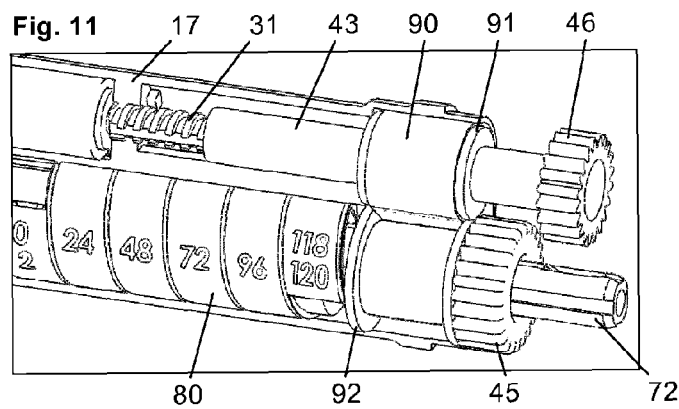
FIG. 11 shows a partial section view of the device of FIG. 9 in a partially assembled state.

Multiple clutch plates increase the torque capacity of the clutch for a given clutch spring force. For the embodiment shown in FIG. 9, force applied to the clutch pack 121, 122 from the clutch spring 125 (FIG. 10a) reduces as the dial grip 71 is depressed, because the upper drive sleeve 42 is pushed by the dial grip 71 together with the cage 123 in the distal direction and away from the proximal housing 12 (FIG. 10b).

In this embodiment, the overall dial grip 71 travel is increased to e.g. 5 mm, 2.5 mm for mechanism disengagement to commence dispense and 2.5 mm for user variable speed control. As the force applied by the clutch spring 125 reduces as the dial grip 71 is depressed, the frictional torque applied to the drive sleeve 41, 42 by the clutch pack 121, 122 also reduces, and the value of the frictional torque is dependent on the axial position of the dial grip 71. The torque available from the spring 90 must overcome the frictional torque of the clutch pack, which reduces the torque applied to the mechanism to dispense a dose. The speed of dispense therefore increases as the user continues to depress the dial grip 71 between the disengagement position and the full travel position. The force required to depress the dial grip 71 increases with its travel due to the combined actions of the spring 110 and clutch spring 125, with spring 110 increasing the resistance despite the weaker spring 125 reducing the resistance.

The facility for removing the need for a user to prime the device when first used is also provided. This involves removing the variable distance (dependant on component and cartridge tolerances) between the cartridge bung 21 and the bearing 33 during manufacture such that the bearing 33 is in contact with, or applying a light load to, the bung 21 when assembled.

This "prime elimination" is achieved using the following method: Rotation of the drive tube 43, independently from the drive sleeve 41, 42, advances the piston rod 30 for prime elimination. Therefore, prior to the proximal housing 12 being fitted, the drive tube 43 is displaced towards the proximal end of the device, so that it no longer engages with the drive sleeve 41, 42 gear teeth 45 (see FIG. 11). The drive tube 43 is then rotated to advance the piston rod 30 and hence its bearing 33 towards the cartridge bung 21. Contact with the bung 21 can either be sensed using measurement of the torque required to rotate the drive tube or by measurement of the axial position of the piston rod 30 relative to the thread 17 in the housing 10. The point at which the piston rod 30 moves to the opposite sides of its threaded engagement with the housing 10 indicates contact with the bung 21.

Figure 12:
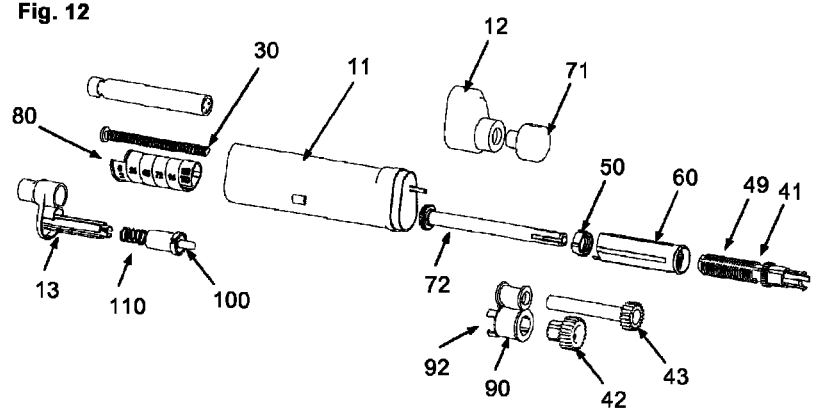
FIG. 12 shows an exploded view of the components of an injection device in accordance with a third embodiment of the present invention.
Figure 13:
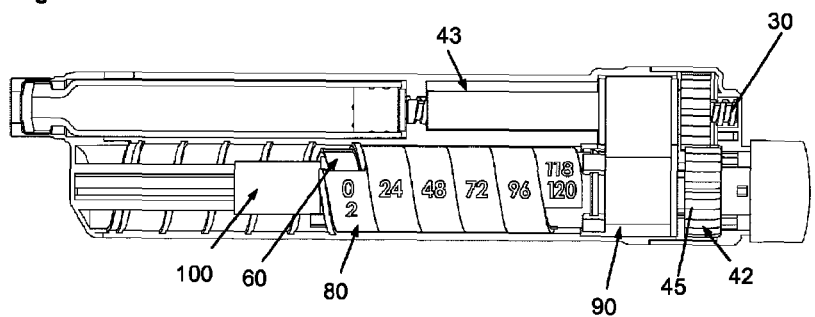
FIG. 13 shows a view of the device of FIG. 11.
Figure 14:
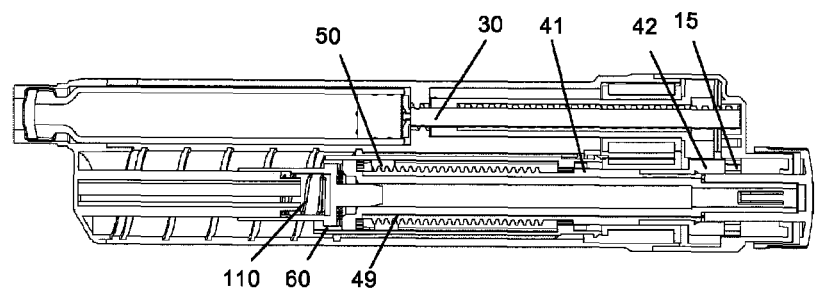
FIG. 14 shows a sectional view of the device of FIG. 11 in the dose setting state.

A third, alternative embodiment is shown in FIGS. 12 to 14. Where appropriate, similar components are given the same reference numerals as in the first embodiment. The design and function of this device is in general very similar to that of the first embodiment. Further, this device is suitable for the speed control of the second embodiment and allows prime elimination as described above.

The main changes with respect to the first embodiment relate to the drive sleeve 41, 42, the dial sleeve 60 and to the nut 50 of the last dose mechanism. Again, the drive sleeve comprises for manufacturing reasons two component parts 41, 42 which are snapped together to behave as a single component. However, the drive sleeve 41, 42 has a prolonged distal part 41 with a threaded section 49. On the other hand, dial sleeve 60 is shorter without the threaded section 61 of the first embodiment. The nut 50, which is a full nut in this embodiment, runs with its inner thread on this threaded section 49. Further, the nut 50 has a splined outer surface which is axially displaceably guided in grooves on the inner surface of dial sleeve 60.

Again, as a user sets a dose, the dial sleeve 60 rotates together with the dial assembly 70, whereas the drive sleeve 41, 42 is coupled to the housing 10 via teeth 15, 45. Thus, nut 50 travels on the threaded section 49. During dose dispensing, the drive sleeve 41, 42, is decoupled from the housing and rotates together with the dial sleeve 60, such that the nut 50 maintains its relative position on the drive sleeve.

Figure 15:
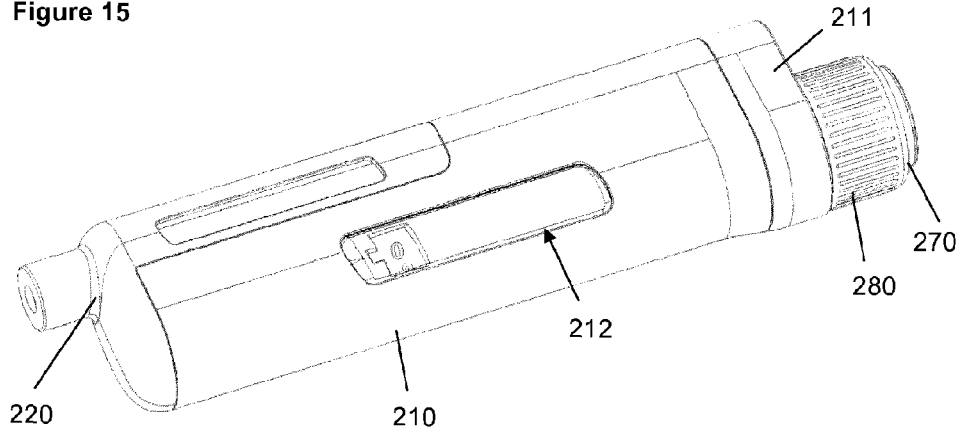
FIG. 15 shows a perspective view of an injection device in accordance with a fourth embodiment of the present invention.
Figure 16:
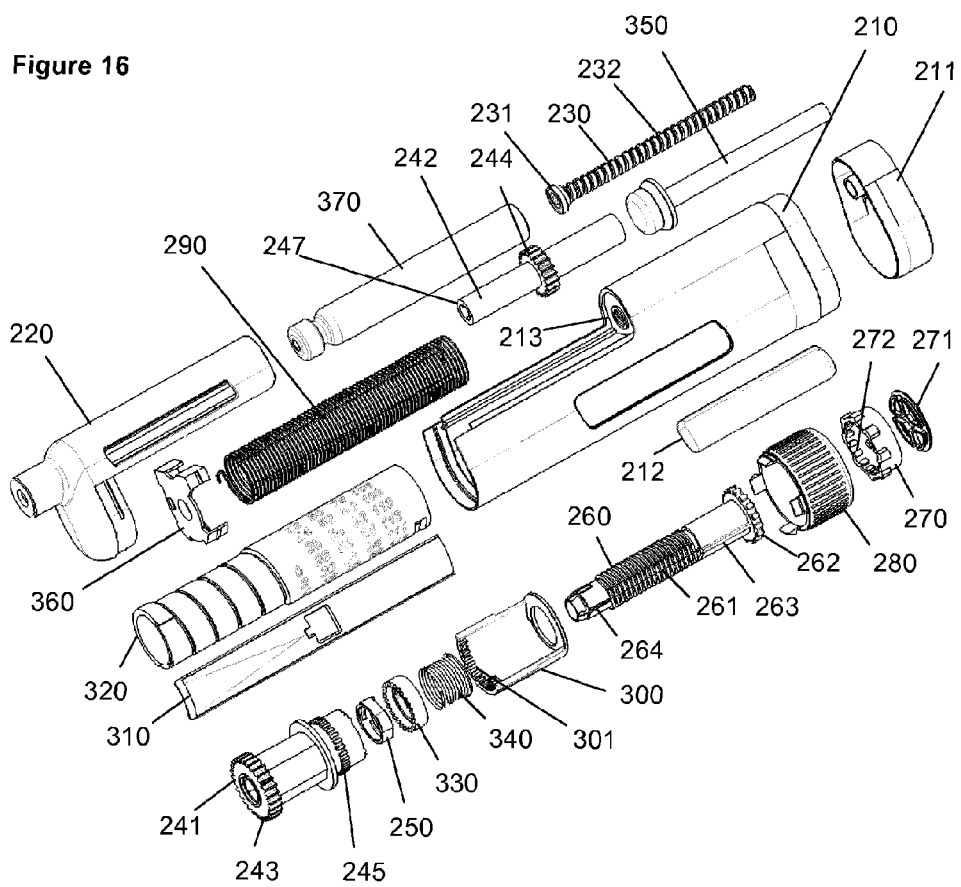
FIG. 16 shows an exploded view of the components of the device of FIG. 15.

A fourth embodiment is shown in FIGS. 15 to 18. FIG. 15 shows a drug delivery device in the form of an injection pen. The device has a distal end (lower left end in FIG. 15) and a proximal end (upper right end in FIG. 15). The component parts of the drug delivery device are shown in FIG. 16. The drug delivery device comprises a housing 210, a cartridge holder 220, a lead screw (piston rod) 230, a driver 241, 242, a nut 250, a dial sleeve 260, a button 270, a dose selector 280, a torsion spring 290, a locking arm 300, a gauge element 310, a dose indicator (number sleeve) 320, a clutch plate 330, a clutch spring 340, a click activator 350, a drive spring retainer 360 and a cartridge 370. A needle arrangement (not shown) with a needle hub and a needle cover may be provided as additional components, which can be exchanged as explained above.

The housing 210 or body is a generally tubular element with an elongate cross-section. In this embodiment all components are located within the main housing 210 component, concentrically mounted about one of two, parallel axes I, II of the mechanism. A body cap 211 is snapped, press-fitted, and/or glued or welded onto the proximal end of main housing 210. Further, a lens 212 is inserted in an elongate aperture of main housing 210. The main housing 210 has a threaded inner wall 213 (web) for receiving piston rod 230. In addition, the housing 210 provides location for the liquid medicament cartridge 370 and cartridge holder 220, a housing cap (not shown), drive spring retainer 360, an interface to rotationally constrain the locking arm 300 and a feature on its external surface to axially retain the dial grip 280.

The cartridge holder 220 is the distal part of the housing and may be snapped, press-fitted, and/or glued or welded onto the distal end of main housing 210. The cartridge holder 220 receives the cartridge 370 and has a distal opening for attachment of the needle and a window or aperture allowing a user to see the cartridge.

The piston rod 230 has a bearing 231 on its distal end, which may be axially constrained to the piston rod 230 and acts on the bung within the liquid medicament cartridge 370. The piston rod 230 is a lead screw with an outer thread 232 for engagement with the threaded inner wall 213 and is rotationally constrained to the drive tube 242 via a splined interface. When rotated, the piston rod 230 is forced to move axially relative to the drive tube 242, through its threaded interface 213, 232 with the housing 210.

In the exemplary embodiment, the driver comprises two components, a drive sleeve 241 and a drive tube 242, which are located on the offset parallel axes I, II. The drive sleeve 241 extends from an interface (proximal face teeth) with the dial sleeve 260 (via the clutch plate 330) to a gear toothed engagement (pinions 243, 244) to the drive tube 242, and incorporates a spline toothed interface 245 with the locking arm 300. Further, drive sleeve 241 comprises splines on its inner surface for engaging nut 250. The drive tube 242 is in gear toothed engagement to the drive sleeve 241 and is splined to the piston rod 230 via splines 247 on its inner surface. The drive tube 242 is fixed axially relative to both the housing 10 and drive sleeve 241.

The last dose nut 250 is located between the dial sleeve 260 and the drive sleeve 241. It is rotationally constrained to the drive sleeve 241, via a splined interface. It moves along a helical path relative to the dial sleeve 260, via a threaded interface, when relative rotation occurs between the dial sleeve 260 and drive sleeve 241 (i.e., during dialing).

The dial sleeve 260 is a dose dial member with a tubular form having an external thread 261 engaging the nut 250, a set of clutch spline teeth 262 at its proximal end for engagement with dose button 270 and splines 263 for engagement with clutch plate 530. Further splines 264 interact with corresponding grooves of the number sleeve 320.

The dose button 270 is permanently splined to the dial grip 280 via outer teeth 272 and splined to the dial sleeve 260 when the dose button 270 is not pressed. This spline interface with the dial sleeve 260 is disconnected when the dose button 270 is pressed.

The dial grip 280 is axially, but not rotationally constrained to the housing 210. It is rotationally constrained, via the splined interface, to the dose button.

The drive spring 290 is attached at one end to the drive spring retainer 360 (which forms part of the housing with the main housing 210) and at the other end to the number sleeve 320. The drive spring 290 is a torsion spring pre-wound upon assembly, such that it applies a torque to the number sleeve 320 when the mechanism is at zero units dialed. The action of rotating the dial grip 280, to set a dose, rotates the number sleeve 320 relative to the housing 210, and further charges the drive spring 290.

The locking arm 300 is rotationally fixed to the housing 210 but allowed to translate axially. When the dose button 270 is pressed, the locking arm 300 spline teeth 301 are disengaged from the drive sleeve 241 allowing the drive sleeve 241 to rotate.

The gauge element 310 is constrained to prevent rotation, but allow axial translation relative to the housing 210 via a splined interface. It is also in threaded engagement to the number sleeve 320 such that rotation of the number sleeve 320 causes axial translation of the gauge element 310. A window is provided in the gauge element with a distal part and a proximal part of the gauge element extending in the respective directions of the window. The outer surface of these parts has a different design, for example in the embodiment of FIG. 16 a triangle is printed on the distal part.

The number sleeve 320 is rotationally constrained, via a splined interface, to the dial sleeve 260. Both components are constrained to the housing 210 to allow rotation, but not translation. The number sleeve 320 is marked with a sequence of numbers, which are visible through the gauge element 310 and a lens 212, located in a slot in the housing 210, to denote the dialed dose of medicament. A zero dose abutment feature and a maximum dose abutment feature are provided as rotational hard stops. Further, there is an end of dose clicker arm at the distal end of number sleeve 320.

The clutch plate 330 is splined to the dial sleeve 260. It is also coupled to the drive sleeve 241 via a ratchet interface (via teeth 331), which occurs on an axial abutment. The ratchet provides a detented position between the dial sleeve 260 and drive sleeve 241 corresponding to each dose unit, and engages different ramped tooth angles during clockwise and anti-clockwise relative rotation.

The clutch spring 340 acts between the clutch plate 330 and the locking arm 300 to force the spline teeth into engagement with the drive sleeve 241 and to force the ratchet between the clutch plate 330 and the drive sleeve 241 together. The axial position of the locking arm 300, clutch plate 330 and dose button 270 are defined by the action of the clutch spring 340. In the "at rest" position, this ensures that the dose button 270 splines are engaged with the dial sleeve 260 and that the drive sleeve 241 spline teeth are engaged with the locking arm 300.

The click activator 350 is axially constrained to the button cap 271 and moves the end of dose clicker arm outwards radially when the dose button 270 is depressed.

The drive spring retainer 360 is held within housing 210 and receives the distal end of drive spring 290. In the embodiment of FIG. 16 the retainer is shown as a separate component part, however, the retainer may as well be an integral part of the housing 210.

With the device in the 'At Rest' condition, the zero dose abutment feature of the number sleeve 320 is positioned against a corresponding zero dose abutment stop of the gauge element 310 and the dose button 270 is not depressed. Dose marking '0' on the number sleeve 320 is visible through the window (lens 212) of the housing 210 and the window of gauge element 310. The drive spring 290, which has a number of pre-wound turns applied to it during assembly of the device, applies a torque to the number sleeve 320 and is prevented from rotating further by the zero dose abutment. It is also possible to "back-wind" the mechanism slightly due to an offset between the zero dose stop and the angular offset of the drive sleeve 241 spline teeth. This has the effect of preventing possible weeping of medicament when a dose is dialed and the zero dose abutment is disengaged.

The user selects a variable dose of liquid medicament by rotating the dial grip 280 clockwise, which generates an identical rotation in the dial sleeve 260 and hence number sleeve 320. Rotation of the number sleeve 320 causes charging of the drive spring 290, increasing the energy stored within it. As the number sleeve 320 rotates, the gauge element 310 translates axially due to its threaded engagement thereby showing the value of the dialed dose. The gauge element 310 has flanges either side of the window area which may have visual differentiation to provide additional feedback as to the dialed/delivered dose value and which obscure those numbers that would be visible in the body slot that do not correspond to the dialed dose display. The dial grip 280 has an increased diameter relative to the housing 210 which aids dialing. This is especially important for an auto-injector mechanism where the stored energy source is charged during dose setting.

The drive sleeve 241 is prevented from rotating, due to the engagement of its splined teeth with the locking arm 300. Relative rotation must therefore occur between the clutch plate 330 and drive sleeve 241 via the dialing ratchet interface.

The user torque required to rotate the dial grip 280 is a sum of the torque required to wind up the drive spring 290, and the torque required to overhaul the dialing ratchet feature. The clutch spring 340 is designed to provide an axial force to the ratchet feature and to bias the clutch plate 330 against the drive sleeve 241. This axial load acts to maintain the ratchet teeth engagement (teeth 331) of the clutch plate 330 and drive sleeve 241. The torque required to overhaul the ratchet is resultant from the axial load applied by the clutch spring 340, the clockwise ramp angle of the ratchet, the friction coefficient between the mating surfaces and the mean radius of the ratchet features.

As the user rotates the dial grip 280 sufficiently to increment the mechanism by one unit, the dial sleeve 260 rotates relative to the drive sleeve 241 by one ratchet tooth. At this point the ratchet teeth 331 re-engage into the next detented position. An audible click is generated by the ratchet re-engagement, and tactile feedback is given by the change in torque input required.

Relative rotation of the dial sleeve 260 and the drive sleeve 241 also causes the last dose nut 250 to travel along its threaded path, towards its last dose abutment on the dial sleeve 260.

With no user torque applied to the dial grip 280, the dial sleeve 260 is now prevented from rotating due to the action of the torque applied by the drive spring 290, solely by the ratchet engagement (teeth 331) between the clutch plate 330 and the drive sleeve 241. The torque necessary to overhaul the ratchet in the anti-clockwise direction is resultant from the axial load applied by the clutch spring 340, the anti-clockwise ramp angle of the ratchet, the friction coefficient between the mating surfaces and the mean radius of the ratchet features. The torque necessary to overhaul the ratchet must be greater than the torque applied to the dial sleeve 260 (and hence clutch plate 330) by the drive spring 290. The ratchet ramp angle is therefore increased in the anti-clockwise direction to ensure this is the case whilst ensuring the dial-up torque is as low as possible.

The user may now choose to increase the selected dose by continuing to rotate the dial grip 280 in the clockwise direction. The process of overhauling the ratchet interfaces between the dial sleeve 260 and drive sleeve 241 is repeated for each dose unit. Additional energy is stored within the drive spring 90 for each dose unit and audible and tactile feedback is provided for each unit dialed by the re-engagement of the ratchet teeth. The torque required to rotate the dial grip 280 increases as the torque required to wind up the drive spring 290 increases. The torque required to overhaul the ratchet in the anti-clockwise direction must therefore be greater than the torque applied to the dial sleeve 260 by the drive spring 290 when the maximum dose has been reached.

If the user continues to increase the selected dose until the maximum dose limit is reached, the number sleeve 320 engages with its maximum dose abutment on the gauge element 310, which prevents further rotation of the number sleeve 320, dial sleeve 260, clutch plate 330 and dial grip 280.

Depending on how many units have already been delivered by the mechanism, during selection of a dose, the last dose nut 250 may contact its last dose abutment with the dial sleeve 260, which is shown in FIG. 18 as a landing on dial sleeve 260 between threads 261 and splines 263. The abutment prevents further relative rotation of the dial sleeve 260 and the drive sleeve 241, and therefore limits the dose size that can be selected. The position of the last dose nut 250 is determined by the total number of relative rotations between the dial sleeve 260 and drive sleeve 241, which have occurred each time the user sets a dose.

With the mechanism in a state in which a dose has been selected, the user is able to deselect any number of units from this dose. Deselecting a dose is achieved by the user rotating the dial grip 280 anti-clockwise.

The torque applied by the drive spring 290 on the mechanism is in the anti-clockwise direction, therefore the torque required from the user on the dial grip 280 to deselect a dose is that to overhaul the ratchet between the clutch plate 330 and drive sleeve 241 in the anti-clockwise direction less the drive spring 290 torque at that particular number sleeve 320 rotational position.

When the ratchet is overhauled, anti-clockwise rotation occurs in the dial sleeve 260 (via the clutch plate 330), which returns the number sleeve 320 towards the zero dose position, and unwinds the drive spring 290. The relative rotation between the dial sleeve 260 and drive sleeve 241 causes the last dose nut 250 to return along its helical path, away from the last dose abutment on the dial sleeve 260.

With the mechanism in a state in which a dose has been selected, the user is able to activate the mechanism to commence delivery of a dose. Delivery of a dose is initiated by the user depressing the dose button 270 on the top of the device.

When the dose button 270 is depressed, its splined engagement with the dial sleeve 260 is disengaged, rotationally disconnecting the dose button 270 and hence dial grip 280 from the delivery mechanism so that the dial grip 280 does not rotate during dispense. The dose button 270 acts on the locking arm 300, which travels axially disconnecting the splined tooth engagement to the drive sleeve 241. The drive sleeve 241 can now rotate and is driven by the drive spring 290 via the number sleeve 320, dial sleeve 260 and clutch plate 330. Rotation of the drive sleeve 241 causes the drive tube 242 to rotate, which in turn causes the piston rod 230 to rotate due to their splined engagement. The piston rod 230 then advances due to its threaded engagement to the housing 210. The number sleeve 320 rotation also causes the gauge element 310 to traverse axially back to its zero position whereby the zero dose abutment stops the mechanism as shown in FIG. 17.

Audible feedback during delivery is provided via a compliant cantilever dispense clicker arm 302 integrated into the locking arm 300, which interfaces axially with the spline teeth 245 of the drive sleeve 241. The spline teeth spacing corresponds to the drive sleeve 241 rotation required for a single dispense unit. During dispense, as the drive sleeve 241 rotates, the spline features 245 engage with the dispense clicker arm 302 to produce an audible click with each dose unit delivered.

Delivery of a dose continues via the mechanical interactions described above while the user continues to depress the dose button 270. If the user releases the dose button 270, the clutch spring 340 returns the dose button 270 to its 'at rest' position via the locking arm 300 and clutch plate 330, the drive sleeve 241 and hence drive tube 242 become rotationally constrained, and delivery of a dose is halted.

During delivery of a dose, the drive sleeve 241 and dial sleeve 260 rotate together, so that no relative motion in the last dose nut 250 occurs. The last dose nut 250 therefore travels towards its abutment on the dial sleeve 260 during dialing only.

Once the delivery of a dose is stopped by the number sleeve 320 returning to the zero dose abutment, the user may release the dose button 270, which will re-engage the locking arm 300 spline teeth 301 with teeth 245 of the drive sleeve 241. The mechanism is now returned to the 'at rest' condition.

It is possible to angle the spline teeth 245, 301 on either the drive sleeve 241 and/or the locking arm 300 so that when the dose button 270 is released the re-engagement of the spline teeth fractionally 'backwinds' the drive sleeve 241 thereby removing the engagement of the number sleeve 320 to the gauge element 310 zero dose stop abutment. This removes the effect of clearances in the mechanism (for example due to tolerances) which could otherwise lead to slight advancement of the piston rod 230 and medicament dispense when the device is dialed for the subsequent dose (due to the number sleeve 320 zero dose stop no longer restraining the mechanism and instead the restraint returning to the splines between the drive sleeve 241 and gauge element 310).

At the end of dose, additional audible feedback is provided in the form of a click (distinct from the dispense clicks) that informs the user that the dispense mechanism has returned to the zero position via the interaction of three components: number sleeve 320, gauge element 310 and click activator 350. The embodiment allows feedback to only be produced at the end of dose delivery (when the dose button 270 is depressed) and not when the device is being dialed into, or away from, the zero position.

When the dose button 270 is not depressed (i.e. during dialing), the end of dose clicker arm is sub-flush with the number sleeve 320 outer surface, and so is clear of the gauge element 310 as the device is dialed into, or away from, the zero position, hence no end of dose click can be produced. When the dose button 270 is depressed (i.e. during dispense), the click activator 350 is moved axially so that it forces the end of dose clicker arm radially outwards.

Usually, the gauge element 310 would conceal the number sleeve 320 and its arm at least partly. As the number sleeve 320 rotates towards the zero position during dispense, the deflected end of dose clicker arm contacts the gauge element 310 at around six units. This causes a preload to be generated in the clicker arm in the radial direction. The drive spring 290 is sufficiently strong to overcome the additional friction caused by the interference between gauge element 310 and the end of dose clicker arm tip. This preload is maintained as the tip of the end of dose clicker arm is in contact with the gauge element 310 up to a point just prior to zero unit position. At this point the tip of the end of dose clicker arm slides off a feature (not shown) formed locally at the trailing edge of the gauge element 310, producing an audible "click". The end of dose click needs a local feature on the gauge element 310 because otherwise a click would occur on every rotation of the number sleeve 320.

As the dose button 270 needs to be released before the device can be dialed away from the zero unit position, the end of dose clicker arm moves inwards radially as the click activator 350 moves rearwards with the dose button 270 and therefore it cannot interfere with the gauge element 310 during dialing. This ensures the end of dose click is only produced between one and zero units and only during dispense. Independent from the above detailed embodiment, the invention relates to a mechanism for use in a medical device that can be operated to deliver variable, userselectable, doses of medicament from a cartridge, e.g. via a needle. The device is preferably disposable. It is delivered to the user in a fully assembled condition ready for first use.

The mechanism provides separate user interfaces for setting and delivery of a dose. A dose is set by rotating a dial grip 280 located at the end of the housing 210. Delivery of a dose is initiated by pressing a dose button 270 on the end of the dial grip 280. Dose delivery will continue while the dose button 270 remains depressed, until the complete set dose has been delivered. The mechanism provides audible, visual and tactile feedback both on the setting and delivery of each dose.

The mechanism contains a helical drive spring 290 to store energy, which is charged during setting of the dose, by the action of the user rotating the dial grip 280. The spring energy is stored until the mechanism is triggered for dispense at which point the energy stored is used to deliver the medicament from the cartridge to the user.

Any dose size can be selected between zero and a pre-defined maximum, in increments to suit the medicament and user profile. The mechanism permits cancelling of a dose without any medicament being dispensed by rotation of the dial grip 280 in the opposing direction to when selecting a dose.

An alternative fifth embodiment of an injection device 1 is shown in FIG. 19 in an exploded view. The injection device comprises 19 components, excluding the liquid medicament cartridge. In more detail, the device comprises a housing 410, which includes a main housing 411, a proximal cap 412 and a cartridge holder 413, a dial grip 420, a dispense button 430, a dial tube 440, a last dose nut 450, a sleeve-like clicker 460, a dispense spring 470, a dose indicator (dial sleeve) 480, a sliding gauge 490, a drive member 500 including a drive sleeve 501 and a drive tube 502, a motor spring 510, a storage spool 520, a piston rod (lead screw) 530 with a bearing 531, a lens (not shown) and a cap (not shown). Most of the components are located concentrically about one of two principle axes I and II of the mechanism as shown in FIG. 20.

The piston rod 530 is located within the housing 510. The drive member 500 is permanently coupled to the piston rod 530 and the drive member 500 is axially movable between a dose setting position, in which the drive member 500 is rotationally constrained to the housing 410, and a dose dispensing position, in which the drive member 500 is rotationally de-coupled from the housing 410. The power reservoir 510 for driving the drive member 500 comprising a reverse wound flat spiral spring as a power reservoir having a first end attached to the first spool 520 and a second end attached to a second spool, which is axially and rotationally constrained to drive member 500. For example, the second spool is an integral part of drive sleeve 501. In the embodiment shown in the Figures, the second end of the spring 510 comprises a portion of reduced width and a free end portion having an increased width compared with the portion of reduced width, wherein the drive member 500, in more detail drive sleeve 501, comprises a cylindrical spool portion having an axial slot 503 and an adjacent narrow recess.

Preferably, the dose indicator 480 is axially constrained to the housing 410 and rotates during dose setting relative to the housing in either a first direction (increasing a dose) or a second opposite direction (decreasing a dose) and it rotates during dose dispensing relative to the housing in the second opposite direction. The gauge element 490 is at least partly interposed between the housing 410 and the dose indicator 480 and at least partly visible through at least one aperture or window of the housing 410. Further, the gauge element 490 is axially guided within the housing 410 and in threaded engagement with the dose indicator 480 such that rotation of the dose indicator 480 causes an axial displacement of the gauge element 490. The housing 410 has an aperture or window and the gauge element 490 has a further aperture or window, which is positioned with respect to the aperture or window of the housing such that at least a part of the dose indicator 480 is visible through the apertures or windows.

In particular, the apertures may be located on the main housing 411 in a location which is visible to the user during dispense of a dose. This may be close to the distal end of the device. Particularly this may be a location in which the number display of the dose indicator 480 could not feasibly be located. There may also be a plurality of gauge apertures.

In particular there may be two gauge apertures, located on opposite sides of the device This increases the visibility of the analog gauge feature for users with a preference for left handed operation, or those users with a preference to hold the device with an alternative grip. The analog gauge is particularly beneficial as an indicator of the dose position of the device during dispense of a dose. During dispense of a dose the number digit display may be changing too quickly for individual dose position markings to be legible. It may therefore be difficult for the user to understand the rate at which the dose is being dispensed, and the amount of medicament still to be dispensed. The axial motion of the analog gauge, which increasingly covers a further surface as a dose is dispensed, gives a simple visible indicator of the dispense rate and the amount of medicament still be to dispensed during the dispense event.

The injection device comprises a limiter mechanism defining a maximum settable dose and a minimum settable dose. The limiter mechanism may comprise a first rotational stop on the dose indicator 480 and a first counter stop on the gauge element 490, which abut in the minimum dose (zero) position, and a second rotational stop on the dose indicator 480 and a second counter stop on the gauge element 490, which abut in the maximum dose position.

The dispense button 430 is axially displaceable and located surrounded by the dial grip 420 which is axially constrained to the housing 410. The clicker sleeve 460 is rotationally constrained to the housing 410 and is axially displaceable relative to the housing between a proximal dose setting position and a distal dose dispensing position. Further, the clicker sleeve 460 comprises teeth releasably engaging corresponding teeth of the dial sleeve 440 which is rotatable during dose setting. The dose indicator 480 may comprise a flexible clicker arm, which is displaceable by the clicker sleeve 460 in a first direction and only during dose dispensing when the device reaches its minimum dose (zero) position in a second, opposite direction by a protruding section of the gauge element 490.

The injection device may further comprise a last dose protection mechanism for preventing the setting of a dose, which exceeds the amount of liquid left in a cartridge. This last dose protection mechanism comprises the nut member 450 located interposed between the clicker sleeve 460 and the dial sleeve 440.

In the injection device the first spool 520 is located concentrically with the piston rod 530 on the first longitudinal axis I, and the second spool, i.e. the drive sleeve 501, is located on a second longitudinal axis II, wherein the first longitudinal axis I is parallel to and spaced from the second longitudinal axis II. As mentioned above, the drive member 500 may comprise the drive tube 502 which is rotatable about the first longitudinal axis I and the drive sleeve 501 which is rotatable about the second longitudinal axis II. The drive sleeve 501 is axially movable between the dose setting position, in which the drive sleeve 501 is rotationally constrained to the housing 410, and the dose dispensing position, in which the drive sleeve 501 is rotationally de-coupled from the housing 410. The drive tube 502 may be permanently rotationally coupled to the drive sleeve 501 or at least if the drive sleeve 501 is in its dose dispensing position.

A clutch 483, 505 is provided interposed between the dose indicator 480 and the drive member 500, wherein the clutch 483, 505 allows relative rotational movement between the dose indicator 480 and the drive member 500 during dose setting and prevents relative rotational movement between the dose indicator 480 and the drive member 500 during dose dispensing. As shown in FIG. 19, the clutch comprises a ring of teeth 505 on the distal side of drive sleeve 501 and inner splines 483 on the dose indicator. The drive sleeve 501 further has a ring of teeth 506 at its proximal end which mesh with corresponding teeth on the drive tube 502. In addition, teeth 506 couple the drive sleeve 501 rotationally to the housing in the (proximal) dose setting position of the drive sleeve 501.

The invention claimed is:

1. A handheld injection device comprising:
a housing;
a piston rod located within the housing, the piston rod defining a first longitudinal axis and being configured to move along the first longitudinal axis to dispense a dose of a medicament during dose dispensing;
a driver coupled to the piston rod, wherein the driver comprises a drive sleeve rotatable about a second longitudinal axis during the dose dispensing and coupled to a flat spiral spring, the drive sleeve being configured to be rotationally restrained to the housing during dose setting; and
a dose setting mechanism comprising a user operable portion positioned at least partially outside of the housing and protruding in a proximal direction from a proximal end of the housing, the user operable portion rotatable about the second longitudinal axis during the dose setting and axially movable along the second longitudinal axis to initiate the dose dispensing, the second longitudinal axis being spaced apart from and parallel to the first longitudinal axis.

2. The injection device of claim 1, wherein the flat spiral spring has a first end and a second end, the first end being attached to a first spool located on the first longitudinal axis, the second end being attached to a second spool located on the second longitudinal axis, and at least one of the first end and the second end being coupled to the driver.

3. The injection device of claim 1, wherein the driver comprises a drive tube rotatable about the first longitudinal axis and directly coupled to the piston rod.

4. The injection device of claim 1, wherein:
the dose setting mechanism comprises a dial assembly and a dial sleeve, the dial assembly and the dial sleeve being rotatable about the second longitudinal axis, and the dial sleeve being configured to be decoupled from the driver during the dose setting and to be coupled to the driver during the dose dispensing, and
the dial assembly comprises the user operable portion.

5. The injection device of claim 1, further comprising a number sleeve threadedly engaged with the housing and splined to the dose setting mechanism.

6. The injection device of claim 1, wherein:
the piston rod comprises a threaded lead screw, and
the housing has a threaded portion configured to cooperate with a threaded outer surface of the piston rod so that rotation of the piston rod axially displaces the piston rod along the first longitudinal axis.

7. The injection device of claim 1, comprising a limiter mechanism defining a maximum settable dose and a minimum settable dose.

8. The injection device of claim 1, comprising a last dose protection mechanism to inhibit setting of an excess dose exceeding an amount of liquid remaining in a cartridge loaded in the housing.

9. The injection device of claim 1, further comprising a component movable along the second longitudinal axis between a dose setting position, in which the dose setting mechanism is rotatable relative to the housing and relative to the driver, and a dose dispensing position, in which the driver is rotatable relative to the housing, the component forming a portion of at least one of the dose setting mechanism and the driver.

10. The injection device of claim 1, further comprising a clicker configured to produce an audible or tactile first feedback during the dose setting or during the dose dispensing.

11. The injection device of claim 10, wherein the clicker is a first clicker, and the injection device comprises a second clicker configured to produce an audible or tactile second feedback during the dose dispensing when the injection device reaches a minimum settable dose position, the second feedback being distinct from the first feedback.

12. The injection device of claim 1, wherein the injection device is configured such that a length of the injection device before the dose setting and a length of the injection device after the dose setting are substantially equal.

13. The injection device of claim 1, wherein:
the user operable portion comprises a release button axially displaceable along the second longitudinal axis, and
the injection device further comprises a friction mechanism configured to engage the driver to decelerate the driver based on a position of the release button along the second longitudinal axis.

14. The injection device of claim 1, further comprising a cartridge containing a medicament and a movable bung to displace the medicament.

15. The injection device of claim 14, wherein the piston rod comprises a bearing at its end facing the bung, the bearing being configured to abut the bung in an unused delivery state of the injection device.

16. The injection device of claim 1, wherein the first longitudinal axis and the second longitudinal axis are offset relative to a central longitudinal axis of the injection device.

17. A dose dispensing and setting mechanism for an injection device, the dose dispensing and setting mechanism comprising: a piston rod defining a first longitudinal axis, the piston rod being configured to move along the first longitudinal axis to dispense a dose of a medicament during dose dispensing; a driver coupled to the piston rod, wherein the driver comprises a drive sleeve rotatable about a second longitudinal axis during the dose dispensing and coupled to a flat spiral spring, the drive sleeve being configured to be rotationally restrained to a housing of the injection device during dose setting; and a dose setting mechanism comprising a user operable portion positionable at least partially outside of the housing of the injection device and protruding in a proximal direction from a proximal end of the housing of the injection device, the user operable portion rotatable about the second longitudinal axis during the dose setting and axially movable along the second longitudinal axis to initiate the dose dispensing, wherein the first longitudinal axis is spaced apart from and parallel to the second longitudinal axis.

18. The dose dispensing and setting mechanism of claim 17, wherein the flat spiral spring has a first end and a second end, the first end being attached to a first spool located on the first longitudinal axis, the second end being attached to a second spool located on the second longitudinal axis, and at least one of the first end and the second end being coupled to the driver.

19. The dose dispensing and setting mechanism of claim 18, wherein the driver comprises a drive tube rotatable about the first longitudinal axis and directly coupled to the piston rod.

20. The dose dispensing and setting mechanism of claim 17, wherein the first longitudinal axis and the second longitudinal axis are offset relative to a central longitudinal axis of the injection device.

21. A handheld injection device comprising:
a housing;
a piston rod located within the housing, the piston rod defining a first longitudinal axis and being configured to move along the first longitudinal axis to dispense a dose of a medicament during dose dispensing;
a driver coupled to the piston rod; and
a dose setting mechanism comprises a dial assembly and a dial sleeve, the dial assembly and the dial sleeve being rotatable about a second longitudinal axis, the second longitudinal axis being spaced apart from and parallel to the first longitudinal axis,
wherein the dial sleeve is configured to be decoupled from the driver during dose setting and to be coupled to the driver during the dose dispensing,
wherein the dial assembly comprises a user operable portion positioned at least partially outside of the housing and protruding in a proximal direction from a proximal end of the housing, and
wherein the user operable portion is rotatable about the second longitudinal axis during the dose setting and axially movable along the second longitudinal axis to initiate the dose dispensing.

* * * * *